US005720804A

United States Patent [19]
Martin

[11] Patent Number: 5,720,804
[45] Date of Patent: *Feb. 24, 1998

[54] TOP NAIL COAT COMPOSITION

[75] Inventor: Frederick L. Martin, St. John, Ind.

[73] Assignee: Almell, Ltd., Dallas, Tex.

[*] Notice: The term of this patent shall not extend beyond the expiration date of Pat. No. 5,512,273.

[21] Appl. No.: 564,969

[22] Filed: Nov. 30, 1995

Related U.S. Application Data

[63] Continuation-in-part of Ser. No. 332,539, Oct. 31, 1994, Pat. No. 5,512,273.

[51] Int. Cl.$^6$ .................... C09D 101/10; C09D 101/14; A61K 7/043
[52] U.S. Cl. .................... 106/170.2; 106/170.27; 106/170.4; 106/170.52; 106/170.56; 106/171.1; 424/61
[58] Field of Search .................... 106/170.2, 170.27, 106/170.4, 170.52, 170.56, 171.1; 424/61

[56] References Cited

U.S. PATENT DOCUMENTS

| | | | |
|---|---|---|---|
| 2,173,755 | 9/1939 | Fuller | 167/85 |
| 2,400,453 | 5/1946 | Bogin | 106/170.4 |
| 2,824,098 | 2/1958 | Volberg et al. | 260/230 |
| 4,097,589 | 6/1978 | Shansky | 424/61 |
| 4,179,304 | 12/1979 | Rossomando | 106/177 |
| 4,229,227 | 10/1980 | Ikeda et al. | 106/181 |
| 4,301,046 | 11/1981 | Schlossman | 260/16 |
| 4,409,203 | 10/1983 | Gordon et al. | 424/61 |
| 4,421,881 | 12/1983 | Benkendorf et al. | 524/24 |
| 4,649,045 | 3/1987 | Gaske et al. | 424/61 |
| 4,712,571 | 12/1987 | Remz et al. | 132/88.7 |
| 4,740,370 | 4/1988 | Faryniarz et al. | 424/61 |
| 4,747,419 | 5/1988 | Flynn et al. | 132/73 |
| 4,749,564 | 6/1988 | Faryniarz et al. | 424/61 |
| 4,798,720 | 1/1989 | Holder | 424/61 |
| 4,820,509 | 4/1989 | Yamazaki et al. | 424/61 |
| 4,897,261 | 1/1990 | Yamazaki et al. | 424/61 |
| 5,071,639 | 12/1991 | Soyama et al. | 424/61 |
| 5,093,108 | 3/1992 | Pappas et al. | 424/61 |
| 5,102,654 | 4/1992 | Castrogiovanni et al. | 424/61 |
| 5,130,125 | 7/1992 | Martin et al. | 424/61 |
| 5,206,011 | 4/1993 | Pappas et al. | 424/61 |

FOREIGN PATENT DOCUMENTS 0336193   10/1989   European Pat. Off.

OTHER PUBLICATIONS

Baran and Mailbach; *Cosmetics Dermatoloy*, 1st Edition, (1994) no month avail. Martin Dunitz., Ltd., London, U.K., "Nail Varnish" pp. 151–156.

Schlossman, "Manicure Preparations", *Poucher's Perfumes, Cosmetics and Soaps*, vol. 3 Cosmetics, Ninth Edition, (1993) no month avail. Chapman & Hall, London, U.K., pp. 244–258.

"Decorative Cosmetics", *Handbook of Cosmetics Science and Technology*, 1st Edition, (1993) no month avail. Elsevier Science Publishers, Ltd., Oxford, U.K., pp. 121, 160–164.

Schlossman, "Nail Cosmetics", *Cosmetics & Toiletries*, vol. 101, No. 4, pp. 23–24, 26–27, (Apr., 1986).

Schlossman, "Manufacturing Processes for Color Cosmetics", *Cosmetics & Toiletries*, vol. 101, No. 4, pp. 95–98, 100–102 (Apr. 1986).

Schlossman, "Techniques for evaluation of nail enamel", *J. Soc. Cosmet. Chem.*, vol. 32, pp. 43–52 (Jan./Feb. 1981).

Schlossman, "Trends in nail care technology", *Cosmetics & Toiletries*, vol. 96, pp. 51–54 (Apr. 1981).

Schlossman, "Nail polish colorants", *Cosmetics & Toiletries*, vol. 95, pp. 31–33 (Jan. 1980).

Wimmer and Schlossman, "The History of Nail Polish", *Cosmetics & Toiletries*, vol. 107, pp. 115–120, (Sep. 1992).

16th IFSCC Congress, "The Effect of Toluene on the Properties of Suspension Nail Polish", vol. 2, pp. 18–30 (1990).

Schlossman, "Modern nail enamel technology", *J. Soc. Cosmet. Chem.*, vol. 31, pp. 29–36 (Jan./Feb. 1980).

Schlossman and Wimmer, "Advances in nail enamel technology", *J.Soc. Cosmet. Chem.*, vol. 43, pp. 331–337 (Nov./Dec. 1992).

Schlossman and Khamis, "Lower VOC Nailpolish Removers", DCI/Oct. 1992, pp. 32, 35,38,40,95.

Schlossman, "Formulating Ethnic Makeup Products", *Cosmetics & Toiletries*, vol. 110, pp. 59–63, (Oct. 1995).

Peirano, "Other film formers for nail enamels", *American Perfumer and Cosmetics*, vol. 84, pp. 35–36, (Aug. 1969).

Peirano, "Nail Lacquers and Removers", *Cosmetics Science and Technology* Interscience Publishers, Inc., pp. 678–692, (1957) no month avail.

Schlossman, "Nail–enamel resins", *Cosmetic Technology*, pp. 53–55, (Oct. 1979).

Scher, "Clearing Up a Rash Comes from Uncovering Its Cause", *Nails*, pp. 86, 88, (Oct. 1995).

"Nailing Down the Best Polish", *Consumer Reports*, pp. 104–107, (Feb. 1995).

Advertisement by Seche Vite, "What Makes a 'Professional'Product *Professional?*", date unknown.

*Primary Examiner*—David Brunsman
*Attorney, Agent, or Firm*—Sidley & Austin

[57]   ABSTRACT

A top coat nail polish composition, which is at least substantially free of ketones and aromatic solvents as well as formaldehyde containing resins and nitrocellulose, contains at least one cellulose ester, a mixture of aliphatic and cycloaliphatic solvents for the cellulose ester, a plasticizer for the cellulose ester, at least two UV blocking agents having different effective UV wavelength blockage ranges, a smoothing agent, an adhesion promoter, and an alkanol solvent for the smoothing agent and the adhesion promoter.

36 Claims, No Drawings

TOP NAIL COAT COMPOSITION

RELATED APPLICATION

This is a continuation-in-part of U.S. patent application Ser. No. 08/332,539, filed Oct. 31, 1994, now U.S. Pat. No. 5,512,273.

FIELD OF THE INVENTION

The invention relates to a composition for a top coat which can be applied over a coating of nail polish on nails.

BACKGROUND OF THE INVENTION

Nail polish is generally applied to fingernails or toe nails as two or more layers, for example in the form of a base coat layer, one or more pigmented layers, and a top coat. It is generally desirable for each applied coat to be dry before the application of the next coat. However, such drying time substantially increases the total time required for a multi-coat application. It is also desirable that the last coat dry relatively quickly so that the wearer is free to engage in other activities promptly after completing the application of the last coat. However, if the exterior surface of the top coat dries too fast, solvents can be trapped at the interface between the top coat and the previously applied undercoat, reducing the cohesiveness of the previously applied undercoat and also reducing the adherence of the top coat to the previously applied undercoat.

Fuller, U.S. Pat. No. 2,173,755 discloses a nail enamel which spreads easily and dries within one and a half minutes to produce a single layer of a non-tacky, durable film, which is readily removable by ethyl acetate and butyl acetate. The Fuller composition utilized non-explosive esters of cellulose dissolved in organic solvents, e.g., ethyl cellulose or cellulose aceto butyrate dissolved in ethylene dichloride, as a replacement for the previously employed nitrocotton, which is explosive. Fuller used diethylene dioxide as a solvent for resins and plasticizers which were to be added to the cellulose ester/organic solvent mixture.

Rossomando, U.S. Pat. No. 4,179,304, discloses the use of a nail polish composition comprising sucrose acetate isobutyrate, a resin selected from sucrose benzoate and sucrose benzoate with polymeric methyl methacrylate, and a plasticizer selected from organic phthalates, organic adipates and organic phosphates, e.g., butyl benzyl phthalate. An objective of the Rossomando composition was to avoid the use of carcinogenic formaldehyde containing resins which had been previously employed in nail polish compositions. Rossomando also discloses that film forming resins such as nitrocellulose, cellulose propionate, cellulose acetate butyrate, ethyl cellulose and acrylic resins could be blended into his nail polish composition. Rossomando discloses the use of a combination of ethyl acetate, butyl acetate and toluene as the solvents for the isopropyl wet nitrocellulose in the basic composition of his working examples.

Martin et al, U.S. Pat. No. 5,130,125, discloses a nail polish top coat composition for application over wet nail polish which dries quickly to a non-tacky, non-brittle solid coat. The preferred composition is set forth in Example 1 of U.S. Pat. No. 5,130,125 as containing toluene, n-butyl acetate, cellulose acetate butyrate ester 318, cellulose acetate butyrate ester 551, benzophenone-1, butyl benzyl phthalate, polysiloxane copolymer, and isopropyl alcohol. While this Martin et al top coat has many advantages, the use of toluene is considered to be undesirable because it is toxic by ingestion, inhalation, or skin absorption, and may cause mild macrocytic anemia. Accordingly, there is a need for a top nail coat composition which is at least substantially free of aromatic solvents such as toluene.

Also, while the benzophenone-1 in the Martin et al top coat composition is a good UV blocking agent, it does not provide the desired level of UV blocking for the full range of ultraviolet radiation. Accordingly, there is a need for a top nail coat composition which has an enhanced range of UV blockage. Similarly, while the polysiloxane copolymer of the Martin et al composition reduces friction, improves the flow of the top coat composition during application, and improves the levelness and gloss of the surface of the top coat composition upon drying, the adhesion of the top coat to the previously applied coats is not as strong as is desired.

Pappas et al, U.S. Pat. No. 5,206,011, discusses the prior art solvent mixtures for nail enamels and concludes that the complicated character of the nail enamel mixtures of the prior art and the many possible combinations of volatile and nonvolatile components had, until the Pappas et al discovery, made the determination of a proper solvent balance from the perspective of viscosity, solubility of the individual components and the acceptability of the deposited enamel (gloss) in combination with a drying time of less than three minutes virtually impossible. Pappas et al state that prior to their discovery, the identification of the evaporation rates of the individual solvents under various conditions had not removed the uncertainty involved in determining a suitable solvent balance incorporating quick-drying characteristics. Although the desirability of a quick drying nail enamel had been a long-felt need, the rate of drying of the nail enamels of the prior art had been limited by these considerations. Pappas et al further conclude that prior to their discovery, simply incorporating low boiling solvents did not increase the likelihood that an acceptable solvent system for nail enamels would be found or that one could obtain a nail enamel composition which dried in under three minutes.

Pappas et al describe their discovery as being that the use of acetone in certain weight percentages of the nail enamel composition, in combination with numerous solvents which provide acceptable viscosity, creates a consistent quick-drying solvent system which provides a nail enamel with favorable characteristics of drying time, viscosity, gloss, flexibility and durability. Thus, the Pappas et al patent teaches that the only way to make it possible to determine a proper solvent balance, to remove the uncertainty involved in determining a suitable solvent balance incorporating quick-drying characteristics, to increase the likelihood that an acceptable solvent system for nail enamels would be found, or to increase the likelihood that one could obtain a nail enamel composition which dried in under three minutes, would be to employ acetone in the solvent system. The Pappas et al patent further states that the amount of the acetone should be no less than about 4.5%, and preferably no less than 13% by weight. However, significant amounts of acetone can lower the viscosity of the nail enamel composition to such an extent that particulate ingredients are permitted to settle, thus causing an undesirable variation in the composition.

Although the Pappas et al patent does disclose several solvent systems which do not contain acetone, the Pappas et al patent indicates that such non-acetone solvent systems do not meet the criteria. For example, the solvent system #2 (consisting of isopropanol, ethyl acetate, n-butyl acetate, and methylchloroform) employed in Example 3 had a drying time of 3 minutes and 17 seconds under specified conditions including 40% relative humidity, or a drying time of about 4.5 to 5.0 minutes at 50–55% relative humidity. Similarly, the solvent system #3 (consisting of isopropanol, ethyl acetate, and n-butyl acetate) employed in Example 4 had a drying time of 3 minutes and 9 seconds under specified conditions including 40% relative humidity, or a drying time of about 4.5 to 5.0 minutes at 50–55% relative humidity. Also, the solvent system #9 (consisting of isopropanol, ethyl acetate, toluene, n-butyl acetate, methylene chloride, and methylchloroform) employed in Example 10 had a drying time of 3 minutes and 21 seconds under specified conditions including 37% relative humidity, or a drying time of about 4.0 to 5.0 minutes at 50–55% relative humidity.

The Pappas et al patent indicates that even when the minimum amount (4.5%) of acetone was present, the drying time was longer than desirable. Thus, in the solvent system #8 (consisting of acetone, isopropanol, ethyl acetate, toluene, n-butyl acetate, and methylchloroform) employed in Example 9, the composition had a drying time of 2 minutes under specified conditions including a low 24% relative humidity, or a drying time of about 3.0 minutes at 50–55% relative humidity. Thus, the Pappas et al patent teaches that the only way in which the desired objectives can be achieved is to employ at least 4.5% acetone in the nail polish composition.

In contrast to the express teachings of the Pappas et al patent, applicant has discovered that the objectives can be achieved without the use of any ketone, such as acetone.

SUMMARY OF THE INVENTION

A top coat composition in accordance with the present invention is at least substantially free of aromatic solvents, and comprises one or more cellulose esters and a mixture of aliphatic and cycloaliphatic solvents for the cellulose esters.

In a presently preferred composition, the cellulose ester comprises one or more cellulose acetate butyrate esters, and the composition includes a plasticizer for the cellulose esters, at least two UV blocking agents having different effective UV wavelength blockage ranges, a smoothing agent and an adhesion promoter. In a presently preferred nail polish composition, which is free of ketones and aromatic solvents as well as formaldehyde containing resins and nitrocellulose, the cellulose acetate butyrate esters constitute at least 95 weight percent of the total of any film forming polymers present in the composition, and the only liquid solvents present in the composition are aliphatic solvents and cycloaliphatic solvents.

DETAILED DESCRIPTION OF THE INVENTION

The term "liquid solvent" is used herein to include (a) liquid materials which are true solvents in that they dissolve the material introduced thereto, (b) liquid wetting agents, e.g., alcohols, and (c) liquid diluents, while excluding solid materials, e.g., plasticizers and secondary film forming polymers which might have some dissolving or plasticizing effect on the film forming polymer. The terms "liquid" and "solid" indicate the physical state at 70° F. and one atmosphere pressure. Wetting agents can be selected to provide a favorable interaction with the primary film forming polymer. The liquid diluents can be selected to provide the desired solubility characteristics which are consistent with dissolving the film forming polymer.

The cellulose esters which can be employed in the invention as a film forming resin include cellulose esters containing monocarboxylic acid groups of 2 to 4 carbon atoms per group, for example, cellulose acetate, cellulose propionate, cellulose butyrate, cellulose acetate butyrate esters, cellulose isobutyrate, and mixtures of any two or more thereof. The presently preferred cellulose esters are the cellulose acetate butyrate esters. It is presently preferred that the cellulose esters are the only primary film forming polymers present in the composition and that they constitute at least 95, preferably at least 96, and more preferably at least 98, weight percent of the total of all film forming polymers present in the composition, thereby providing a clear nail enamel which is resistant to yellowing.

The solvent for the cellulose esters is a mixture of acyclic aliphatic and cycloaliphatic solvents. It is presently preferred that the solvent for the cellulose esters be a mixture of acyclic aliphatic liquid solvents and cycloaliphatic liquid solvents, wherein the acyclic aliphatic liquid solvents can be linear or branched aliphatic compounds, and wherein the cycloaliphatic liquid solvents can be simple cycloaliphatic compounds without any branches on the rings, or branched cycloaliphatic compounds, e.g., alkylcycloaliphatic compounds, dialkylcycloaliphatic compounds, trialkylcycloaliphatic compounds, tetraalkylcycloaliphatic compounds, etc.

Suitable aliphatic solvents include alkanes having 4 to 10 carbon atoms per molecule, aliphatic esters having 3 to 10 carbon atoms per molecule, alkanols having 2 to 10 carbon atoms per molecule, e.g., n-butane, isobutane, n-pentane, isopentane, hexane, heptane, isoheptane, octane, 3,3-dimethyl hexane, 3-ethyl hexane, nonane, 2,2,3-trimethyl hexane, 2-methyl octane, 3-ethyl-2-methyl hexane, 2,3-dimethyl octane, decane, methyl propionate, methyl acetate, ethyl acetate, n-propyl acetate, n-butyl acetate, isobutyl acetate, sec-butyl acetate, tert-butyl acetate, 1,1-dimethyl butyl acetate, n-propyl formate, ethyl propionate, hexyl acetate, 3-ethyl-3-pentyl acetate, octyl acetate, 2-ethyl hexyl acetate, ethanol, n-propanol, isopropanol, n-butanol, n-pentanol, n-hexanol, n-heptanol, 3-methyl 3-hexanol, 2-ethyl 3-hexanol, n-octanol, n-decanol, and mixtures of any two or more thereof. The presently preferred aliphatic esters are the acyclic hydrocarbyl esters having 3 to 6 carbon atoms per molecule, and the presently preferred alkanols are those having 3 to 6 carbon atoms per molecule. While the alkanes having 4 to 6 carbon atoms per molecule can be utilized in the invention, the presently preferred alkanes are those having 7 to 10 carbon atoms per molecule, and the more preferred are those having 8 to 9 carbon atoms per molecule.

Suitable cycloaliphatic solvents include cycloalkanes having 4 to 10 carbon atoms per molecule, cycloaliphatic esters having 4 to 10 carbon atoms per molecule, cycloalkanols having 4 to 10 carbon atoms per molecule, e.g., cyclobutane, cyclopentane, methyl cyclobutane, cyclohexane, ethyl cyclobutane, methyl cyclopentane, ethyl cyclopentane, propyl cyclopentane, 1,1,2-trimethyl cyclopentane, 1,1-dimethyl cyclohexane, 1,2-dimethyl cyclohexane, 1,3-dimethyl cyclohexane, 1,4-dimethyl cyclohexane, ethyl cyclohexane, propyl cyclohexane, isopropyl cyclohexane, 1,1,3-trimethyl cyclohexane, 1-methyl-4-ethyl cyclohexane, n-butyl cyclohexane, isobutyl cyclohexane, cyclobutanol, cyclobutylcarbinol, cyclopentanol, naphthenes, and mixtures of any two or more thereof. The presently preferred cycloalkanols are those having 4 to 6 carbon atoms per molecule. Similarly, the presently preferred cycloaliphatic esters are those having 4 to 6 carbon atoms per molecule. However, while the cycloalkanes having 4 to 6 carbon atoms per molecule can be employed in the invention, the presently preferred cycloalkanes are the branched and unbranched cycloalkanes having 7 to 10 carbon atoms per molecule, and the more preferred cycloalkanes are those having 8 to 9 carbon atoms per molecule.

In general, the cycloaliphatic solvents will constitute from about 1 to about 20 volume percent, preferably from about 2 to about 15 volume percent, and more preferably from about 3 to about 10 volume percent of the mixture of solvents used to dissolve the cellulose esters. A presently preferred solvent mixture for the cellulose esters comprises about 30 to about 45 volume percent ethyl acetate, about 40 to about 65 volume percent n-butyl acetate, and about 5 to about 20 volume percent naphthenic material. Many of the commercially available naphthenic materials are petroleum refinery product streams composed of acyclic paraffins and cycloparaffins (naphthenes) having from 6 to 10 carbon atoms per molecule, the acyclic paraffins constituting from about 10 to about 90 volume percent of the naphthenic material and the cyclic paraffins constituting about 90 to about 10 volume percent of the naphthenic material, with the aromatic content being less than 1 volume percent. It is presently preferred that at least 70, more preferably at least 80, and even more preferably at least 90, volume percent of the naphthenic material be acyclic paraffins and cycloparaffins containing 8 to 9 carbon atoms per molecule, with the paraffin content being in the range of about 25 to about 90 volume percent and more preferably in the range of about 30 to 50 volume percent, the cycloparaffin content being in the range of about 75 to about 10 volume percent and more preferably in the range of about 50 to about 70 volume percent, and the aromatic content being less than about 0.1 volume percent and more preferably less than about 0.01 volume percent of the naphthenic material. The naphthenic material can be a Naphtholite™ naphthenic material which is available from Union 76 Chemicals as a mixture of paraffins and cycloparaffins containing less than 1 percent aromatics, with the paraffin content being in the range of about 37 to about 50 percent and the cycloparaffin content being in the range of about 62 to about 49 percent, with at least about 90 volume percent of the paraffins and cycloparaffins having 8 to 9 carbon atoms per molecule. The naphthenic material can be a KERMAC™ VM&P Naphtha, Rule 66, which is available from Kerr-McGee Refining Corporation as a light aliphatic solvent naphtha, containing a mixture of acyclic paraffins and cycloparaffins and less than 1 percent aromatics. The naphthenic material can be a light aliphatic solvent naphtha available from Shell Chemical Company as Shell VM&P Naphtha HT™, which is a complex combination of aliphatic hydrocarbons and cycloaliphatic hydrocarbons containing 8 to 9 carbon atoms per molecule with a high naphthene content and less than 0.01 volume percent aromatic hydrocarbons.

The ratio of the cellulose ester solvent mixture to the cellulose esters can be any suitable value, but in general will be in the range of about 10 to about 25 fluid ounces of the solvent mixture per 100 grams of cellulose ester, and preferably will be in the range of about 12 to about 16 fluid ounces of the solvent mixture per 100 grams of cellulose ester.

Any suitable plasticizer for the cellulose esters can be employed in the present top coat composition. Examples include organic phthalates, organic adipates, and organic phosphates, e.g., butyl benzyl phthalate, camphor, dibutyl phthalate, tricresyl phosphate, diethyl phthalate, tributyl phosphate, dibutyl glycolate, dioctyl phthalate, butyl stearate, and mixtures of any two or more thereof. The plasticizer can be employed in any suitable amount, but will in general be employed in an amount in the range of about 0.1 to about 5 fluid ounces per 100 grams of cellulose ester, and preferably will be in the range of about 0.2 to about 1 fluid ounce per 100 grams of cellulose ester.

Any suitable UV blocker can be employed in the present top coat composition. However, it is presently preferred to employ at least two UV blockers having different ranges of UV wavelength blockage so as to extend the protection against UV radiation. Any suitable amount of the UV blockers can be employed, but the total amount of UV blockers will generally be in the range of about 0.1 to about 5 grams per 100 grams of cellulose ester, and preferably will be in the range of about 0.2 to about 1 gram per 100 grams of cellulose ester. The presently preferred UV blockers are benzophenone-1 and benzophenone-3, with the amount of the benzophenone-1 preferably being in the range of about 0.5 to about 0.8 gram per 100 grams of cellulose ester, and the amount of the benzophenone-3 preferably being in the range of about 0.001 to about 0.002 gram per 100 grams of cellulose ester.

In order to provide the desired characteristics of flow and level, the top coat composition can contain a smoothing agent. The smoothing agent reduces friction, improves the flow of the top coat composition during application, and improves the leveless and gloss of the surface of the top coat composition upon drying. Suitable smoothing agents include silicone polymers and copolymers, polyamides, polyacrylamides, and polycarboxylic acids, and mixtures of any two or more thereof. Any suitable amount of smoothing agent can be employed, but the amount will generally be in the range of 0 to about 5 grams per 100 grams of cellulose ester, and preferably will be in the range of about 0.5 to about 3 grams per 100 grams of cellulose ester. The presently preferred smoothing agent is a polysiloxane copolymer.

In order to provide the desired characteristics of adhesion, the top coat composition can contain an adhesion promoter. The adhesion promoter improves the adhesion of the top coat to the previously applied coats. Any suitable amount of adhesion promoter can be employed, but the amount will generally be in the range of 0 to about 5 grams per 100 grams of cellulose ester, and preferably will be in the range of about 0.2 to about 2 grams per 100 grams of cellulose ester. Examples of suitable adhesion promoters which can be employed include sucrose benzoates, sucrose acetate isobutyrates, and aminoalkoxysilanes, with aminomethoxysilane being presently preferred.

In order to facilitate the introduction of the smoothing agent and the adhesion promoter into the top coat composition, it is desirable that these components first be dispersed in a suitable solvent, preferably an alkanol having 2 to 6 carbon atoms per molecule, and the resulting solution then be added to the solution of the cellulose ester in its mixture of solvents. The solvent for the smoothing agent and the adhesion promoter can be employed in any suitable amount, but will in general be employed in an amount in the range of about 0.5 to about 5 fluid ounces per 100 grams of cellulose ester, and preferably will be in the range of about 1 to about 3 fluid ounces per 100 grams of cellulose ester. The presently preferred liquid solvent for the smoothing agent and the adhesion promoter is isopropyl alcohol.

In general, the cycloaliphatic solvents will constitute from about 0.9 to about 18 volume percent, preferably from about 1.8 to about 13.5 volume percent, and more preferably from about 2.7 to about 9 volume percent of the total amount of solvents in the top coat composition, including the alkanol employed to dissolve the smoothing agent and the adhesion promoter.

It is presently preferred that the total amount of solvents in the top coat composition consists of at least one acyclic hydrocarbyl ester having 3 to 6 carbon atoms per molecule, at least one acyclic alkanol having 2 to 6 carbon atoms per molecule, and a mixture of cycloalkanes and acyclic alkanes. In general, the at least one acyclic hydrocarbyl ester will constitute from about 55 to about 95 volume percent, preferably from about 65 to about 90 volume percent, and more preferably from about 75 to about 85 volume percent of the total amount of solvents in the top coat composition; the at least one acyclic alkanol will constitute from about 3 to about 30 volume percent, preferably from about 5 to about 20 volume percent, and more preferably from about 5 to about 15 volume percent of the total amount of solvents in the top coat composition; the mixture of cycloalkanes and acyclic alkanes will constitute from about 2 to about 30 volume percent, preferably from about 5 to about 20 volume percent, and more preferably from about 5 to about 15 volume percent of the total amount of solvents in the top coat composition. In general, the acyclic alkanes will constitute from about 0.6 to about 18 volume percent, preferably from about 1.2 to about 13.5 volume percent, and more preferably about 1.4 to about 9 volume percent of the total amount of solvents in the top coat composition, while the cycloalkanes will constitute from about 0.9 to about 18 volume percent, preferably from about 1.8 to about 13.5 volume percent, and more preferably about 2.7 to about 9 volume percent of the total amount of solvents in the top coat composition. It is presently preferred that substantially all of the mixture of acyclic alkanes and cycloalkanes have from 6 to 10 carbon atoms per molecule, and more preferably from 8 to 9 carbon atoms per molecule.

EXAMPLE I

A top nail coat composition, not containing any cycloparaffins, was prepared with the following ingredients:

| INGREDIENT | AMOUNT |
| --- | --- |
| Ethyl acetate | 40.0 fluid oz. |
| N-butyl acetate | 48.0 fluid oz. |
| Cellulose acetate butyrate ester 381 | 560 grams |
| Cellulose acetate butyrate ester 551 | 80 grams |
| Benzophenone-1 | 4 grams |
| Benzophenone-3 | 0.01 gram |
| Butyl benzyl phthalate | 4.0 fluid oz. |
| Polysiloxane copolymer | 12 grams |
| Aminomethoxysiliane | 1 gram |
| Isopropyl alcohol | 10.0 fluid oz. |

The ethyl acetate and the n-butyl acetate were blended, and then the cellulose acetate butyrate esters were sifted into the blend of the acetate solvents while the resulting mixture was stirred at slow speed in order to avoid agglomeration of the esters. The resulting mixture was then stirred at high speed until the esters had dissolved in the solvent blend. The polysiloxane copolymer, the aminomethoxysilane, and the isopropyl alcohol were admixed together and the resulting admixture was then added to the solution of the cellulose esters in the solvent mixture along with the benzophenone-1, benzophenone-3, and the butyl benzyl phthalate, while the resulting combination was stirred at low speed.

The resulting composition was applied as a top coat over a wet undercoat of nail polish. The exterior surface of the top coat dried in approximately 60 seconds, but the adhesion of the top coat to the undercoat was considered to be inadequate even though the top coat composition contained an adhesion promoter. The problem was considered to have resulted from the presence of a significant amount of solvent at the interface of the top coat and the undercoat when the exterior surface of the top coat was considered dry.

EXAMPLE II

A top nail coat composition, containing cycloparaffins and being at least substantially free of ketones and aromatic solvents as well as formaldehyde containing resins and nitrocellulose, was prepared with the following ingredients:

| INGREDIENT | AMOUNT |
| --- | --- |
| Ethyl acetate | 30.0 fluid oz. |
| N-butyl acetate | 48.0 fluid oz. |
| Naphtholite ™ 66/3 | 10.0 fluid oz. |
| Cellulose acetate butyrate ester 381 | 560 grams |
| Cellulose acetate butyrate ester 551 | 80 grams |
| Benzophenone-1 | 4 grams |
| Benzophenone-3 | 0.01 gram |
| Butyl benzyl phthalate | 4.0 fluid oz. |
| Polysiloxane copolymer | 12 grams |
| Aminomethoxysilane | 1 gram |
| Isopropyl alcohol | 10.0 fluid oz. |

The Naphtholite™ 66/3, obtained from Union 76 Chemicals, is a mixture of approximately 37 weight percent acyclic paraffins, approximately 62 weight percent cycloparaffins, and less than 1% aromatics, and has a flash point of 12.2° C., an initial boiling point of 249° C., and a vapor pressure of 14 mm Hg at 20° C.

The resulting composition was applied as a top coat over a wet undercoat of nail polish. The exterior surface of the top coat dried in approximately 75 seconds, and the adhesion of the top coat to the undercoat was considered to be adequate. Thus, while the presence of the cycloparaffins slightly increased the drying time of the top coat, the drying time was still acceptable, and this permitted the concentration of solvents at the interface of the top coat and the undercoat to be reduced sufficiently so that adequate adhesion of the top coat to the undercoat was achieved. To any extent that either of the aminomethoxysilane and the polysiloxane copolymer could be considered to be a film forming polymer, the cellulose esters would still constitute at least 98 weight percent of the total film forming polymers present in the composition.

Reasonable variations in and modifications to the invention are possible within the scope of the foregoing description and the appended claims.

That which is claimed is:

1. A composition comprising at least one cellulose ester containing monocarboxylic acid groups having from 2 to 4 carbon atoms per group, and a plurality of solvents, wherein a total amount of solvents in said composition consists of at least one aliphatic solvent and at least one cycloaliphatic solvent, the composition being at least substantially free of aromatic solvents;

wherein said at least one aliphatic solvent is selected from the group consisting of alkanes, aliphatic esters, and alkanols; and wherein said at least one cycloaliphatic solvent is selected from the group consisting of cycloalkanes, cycloaliphatic esters, and cycloalkanols.

2. A composition in accordance with claim 1, wherein said at least one cycloaliphatic solvent constitutes from about 0.9 to about 18 volume percent of said total amount of solvents.

3. A composition in accordance with claim 2, wherein said total amount of solvents consists of at least one aliphatic ester having 3 to 6 carbon atoms per molecule, at least one alkanol having 2 to 6 carbon atoms per molecule, and naphthenic material, said naphthenic material consisting essentially of a mixture of alkanes and cycloalkanes and having less than 1 percent aromatics.

4. A composition in accordance with claim 3, wherein said naphthenic material has a paraffin content in the range of about 37 to about 50 percent and a cycloparaffin content in the range of about 62 to about 49 percent.

5. A composition in accordance with claim 4 wherein said at least one aliphatic ester comprises ethyl acetate and n-butyl acetate, and wherein said at least one alkanol comprises isopropanol.

6. A composition in accordance with claim 3, wherein substantially all of said alkanes and said cycloalkanes in said naphthenic material have from 6 to 10 carbon atoms per molecule.

7. A composition in accordance with claim 3, wherein substantially all of said alkanes and said cycloalkanes in said naphthenic material have from 8 to 9 carbon atoms per molecule.

8. A composition in accordance with claim 7 wherein said at least one aliphatic ester comprises ethyl acetate and n-butyl acetate.

9. A composition in accordance with claim 8 wherein said at least one alkanol comprises isopropanol.

10. A composition in accordance with claim 1, wherein said total amount of solvents consists of at least one acyclic hydrocarbyl ester having 3 to 6 carbon atoms per molecule, at least one alkanol having 2 to 6 carbon atoms per molecule, and a mixture of alkanes and cycloalkanes, wherein said mixture has a paraffin content in the range of about 10 to about 90 percent, a cycloparaffin content in the range of about 90 to about 10 percent, and less than 1 percent aromatics.

11. A composition in accordance with claim 10, wherein said at least one acyclic hydrocarbyl ester constitutes from about 55 to about 95 volume percent of said total amount of solvents, wherein said at least one alkanol constitutes from about 3 to about 30 volume percent of said total amount of solvents, and wherein said mixture constitutes from about 2 to about 30 volume percent of said total amount of solvents.

12. A composition in accordance with claim 1, wherein said total amount of solvents consists of at least one acyclic hydrocarbyl ester having 3 to 10 carbon atoms per molecule, at least one acyclic alkanol having 2 to 10 carbon atoms per molecule, at least one acyclic alkane having 4 to 10 carbon atoms, and at least one cycloalkane having 4 to 10 carbon atoms.

13. A composition in accordance with claim 12, wherein said at least one acyclic hydrocarbyl ester constitutes from about 55 to about 95 volume percent of said total amount of solvents, wherein said at least one acyclic alkanol constitutes from about 3 to about 30 volume percent of said total amount of solvents, wherein said at least one acyclic alkane constitutes from about 0.6 to about 18 volume percent of said total amount of solvents, and wherein said at least one cycloalkane constitutes from about 0.9 to about 18 volume percent of said total amount of solvents.

14. A composition in accordance with claim 12, wherein said at least one acyclic hydrocarbyl ester constitutes from about 75 to about 85 volume percent of said total amount of solvents, wherein said at least one acyclic alkanol constitutes from about 5 to about 15 volume percent of said total amount of solvents, wherein said at least one acyclic alkane constitutes from about 1.4 to about 9 volume percent of said total amount of solvents, and wherein said at least one cycloalkane constitutes from about 2.7 to about 9 volume percent of said total amount of solvents.

15. A composition in accordance with claim 14, wherein said acyclic hydrocarbyl ester has from 3 to 6 carbon atoms per molecule, wherein said at least one acyclic alkanol has from 2 to 6 carbon atoms per molecule, wherein substantially all of said at least one acyclic alkane has from 8 to 9 carbon atoms per molecule, and wherein substantially all of said at least one cycloalkane has from 8 to 9 carbon atoms.

16. A composition in accordance with claim 15 wherein said at least one acyclic hydrocarbyl ester comprises ethyl acetate and n-butyl acetate, and wherein said at least one alkanol comprises isopropanol.

17. A composition comprising at least one cellulose ester containing monocarboxylic acid groups having from 2 to 4 carbon atoms per group, and a plurality of solvents including at least one aliphatic solvent and at least one cycloaliphatic solvent, the composition being at least substantially free of ketones and aromatic solvents as well as formaldehyde containing resins and nitrocellulose;

wherein said at least one aliphatic solvent is selected from the group consisting of alkanes, aliphatic esters, and alkanols; and wherein said at least one cycloaliphatic solvent is selected from the group consisting of cycloalkanes, cycloaliphatic esters, and cycloalkanols.

18. A composition in accordance with claim 17, wherein said at least one cellulose ester comprises at least one cellulose acetate butyrate ester, and wherein said cycloaliphatic solvent constitutes from about 0.9 to about 18 volume percent of said plurality of solvents.

19. A composition in accordance with claim 17, wherein said at least one cellulose ester constitutes at least 95 weight percent of the total of all film forming polymers in said composition.

20. A composition in accordance with claim 17, wherein the total amount of solvents in said composition consists essentially of said at least one aliphatic solvent and said at least one cycloaliphatic solvent.

21. A composition in accordance with claim 17, wherein said at least one cycloaliphatic solvent constitutes from about 1.8 to about 13.5 volume percent of said plurality of solvents.

22. A composition in accordance with claim 17, wherein said total amount of solvents consists essentially of at least one acyclic hydrocarbyl ester having 3 to 6 carbon atoms per molecule, at least one alkanol having 2 to 6 carbon atoms per molecule, and a mixture of alkanes and cycloalkanes, wherein said mixture has a paraffin content in the range of about 10 to about 90 percent, a cycloparaffin content in the range of about 90 to about 10 percent, and less than 1 percent aromatics.

23. A composition in accordance with claim 22, wherein said at least one acyclic hydrocarbyl ester constitutes from about 55 to about 95 volume percent of said total amount of solvents, wherein said at least one alkanol constitutes from about 3 to about 30 volume percent of said total amount of solvents, and wherein said mixture constitutes from about 2 to about 30 volume percent of said total amount of solvents.

24. A composition in accordance with claim 17, wherein said total amount of solvents consists essentially of at least one acyclic hydrocarbyl ester having 3 to 10 carbon atoms per molecule, at least one acyclic alkanol having 2 to 10 carbon atoms per molecule, at least one acyclic alkane having 4 to 10 carbon atoms, and at least one cycloalkane having 4 to 10 carbon atoms.

25. A composition in accordance with claim 24, wherein said at least one acyclic hydrocarbyl ester constitutes from about 55 to about 95 volume percent of said total amount of solvents, wherein said at least one acyclic alkanol constitutes from about 3 to about 30 volume percent of said total amount of solvents, wherein said at least one acyclic alkane constitutes from about 0.6 to about 18 volume percent of said total amount of solvents, and wherein said at least one cycloalkane constitutes from about 0.9 to about 18 volume percent of said total amount of solvents.

26. A composition in accordance with claim 24, wherein said at least one acyclic hydrocarbyl ester constitutes from about 75 to about 85 volume percent of said total amount of solvents, wherein said at least one acyclic alkanol constitutes from about 5 to about 15 volume percent of said total amount of solvents, wherein said at least one acyclic alkane constitutes from about 1.4 to about 9 volume percent of said total amount of solvents, and wherein said at least one cycloalkane constitutes from about 2.7 to about 9 volume percent of said total amount of solvents.

27. A composition in accordance with claim 26, wherein said acyclic hydrocarbyl ester has from 3 to 6 carbon atoms per molecule, wherein said at least one acyclic alkanol has from 2 to 6 carbon atoms per molecule, wherein substantially all of said at least one acyclic alkane has from 8 to 9 carbon atoms per molecule, and wherein substantially all of said at least one cycloalkane has from 8 to 9 carbon atoms.

28. A composition in accordance with claim 27 wherein said at least one acyclic hydrocarbyl ester comprises ethyl acetate and n-butyl acetate, and wherein said at least one alkanol comprises isopropanol.

29. A composition in accordance with claim 28, wherein said at least one cellulose ester constitutes at least 96 weight percent of the total of any film forming polymers in said composition.

30. A composition in accordance with claim 17, further comprising a plasticizer for said at least one cellulose ester, and at least one UV blocking agent.

31. A composition in accordance with claim 30, wherein said at least one cycloaliphatic liquid solvent constitutes from about 1.8 to about 13.5 volume percent of the total amount of liquid solvents in said composition.

32. A composition in accordance with claim 31, further comprising a smoothing agent and an adhesion promoter, wherein said smoothing agent improves levelness and gloss of a surface of the composition upon drying, and wherein said adhesion promoter improves adhesion of the composition to any previously applied coats.

33. A composition in accordance with claim 30, wherein said at least one cellulose ester comprises at least one cellulose acetate butyrate ester which constitutes at least 96 weight percent of the total of all film forming polymers present in said composition.

34. A composition in accordance with claim 30, wherein said at least one UV blocking agent comprises at least two UV blocking agents having effective UV wavelength blockage ranges which are different from each other.

35. A composition consisting essentially of:
   at least one cellulose acetate butyrate ester,
   a plurality of liquid solvents including at least one aliphatic liquid solvent and at least one cycloaliphatic liquid solvent,
   a plasticizer for said at least one cellulose acetate butyrate ester, and
   at least one UV blocking agent,
   wherein the composition is at least substantially free of ketones and aromatic solvents as well as formaldehyde containing resins and nitrocellulose,
   wherein said at least one aliphatic liquid solvent is selected from the group consisting of alkanes, aliphatic esters, and alkanols;
   wherein said at least one cycloaliphatic liquid solvent is selected from the group consisting of cycloalkanes, cycloaliphatic esters, and cycloalkanols; and
   wherein said at least one cycloaliphatic liquid solvent constitutes from about 0.9 to about 18 volume percent of said plurality of liquid solvents.

36. A composition in accordance with claim 35, further including a smoothing agent and an adhesion promoter, wherein said smoothing agent improves levelness and gloss of a surface of the composition upon drying, wherein said adhesion promoter improves adhesion of the composition to any previously applied coats.

* * * * *